United States Patent [19]

Kirmann

[11] Patent Number: Plant 6,015

[45] Date of Patent: Sep. 15, 1987

[54] GERANIUM PLANT NAMED SHIRLEY

[75] Inventor: Wolfgang Kirmann, Langenzersdorf, Austria

[73] Assignee: Mirko Vavra, Bisamberg, Austria

[21] Appl. No.: 810,673

[22] Filed: Dec. 19, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A geranium plant named Shirley having bright red flower color; compact, self-branching growth habit; early flowering; good bud production at night temperatures up to 16° C., thus providing a long and continuous flowering period; and ease of propagation and good rooting habit.

2 Drawing Figures

The present invention comprises a new and distinct cultivar of geranium, botanically known as *Pelargonium domesticum,* and hereinafter referred to by the cultivar name Shirley.

Shirley is a product of a planned breeding program which had the objective of creating new geranium cultivars having compact growth habit, early flowering, abundant flower production, long lasting flowers, and bright red flower color.

Shirley was originated from a hybridization made by applicant in a controlled breeding program in Bisamberg, Austria in 1980. The female parent was Wiener Blut, a cultivar characterized by its strong growth habit, early flowering and orange-red flower color. The male parent of Shirley was a cultivar designated as seedling 314/79, having a strong compact growth habit, early flowering and orange-red flower color, but characterized by smaller foliage and flowers.

Shirley was discovered and selected as one flowering plant within the progeny of the stated cross by applicant on Mar. 15, 1981 in a controlled environment in Bisamberg, Austria.

The first act of asexual reproduction of Shirley was accomplished when vegetative cuttings were taken from the initial selection on Aug. 30, 1981 in a controlled environment in Bisamberg, Austria by a technician working under formulations established and supervised by Wolfgang Kirmann. Horticultural examination of selected units initiated in the spring of 1982 has demonstrated that the combination of characteristics as herein disclosed for Shirley are firmly fixed and are retained through successive generations of asexual reproduction.

Shirley has not been observed under all possible environmental conditions. The phenotype may vary significantly with variations in environment such as temperature, light intensity, and day length. The following observations, measurements and comparisons describe plants grown in Bisamberg, Austria under conditions which approximate those generally used in commercial practice.

The following traits have been repeatedly observed and are determined to be basic characteristics of Shirley, which in combination distinguish this geranium as a new and distinct cultivar.

1. A totally new bright red flower color.
2. Early flowering and long flowering period.

3. Compact, self-branching growth habit, resulting in the setting of many buds.
4. Propagates well with good rooting habit.
5. Buds are produced under normal greenhouse conditions (5000 Lux for 16 hours per day) at 14°–16° C. This is well above the cooler temperatures required for previous Domesticum varieties. In addition, plants flowered indoors can be transplanted outdoors and will continue blooming at night temperatures as high as 16° C. Known Domesticum cultivars will produce buds outdoors only at night temperatures of 10° C. or lower.
6. Shirley is unique with regard to the combined features of compactness, continuous flowering, floriferous habit, and red flower color.

Of the many commercial cultivars known to the present inventor, the most similar in comparison to Shirley is Knauffs Leuchtfeuer, an unpatented but commercial cultivar. In comparison to Knauffs Leuchtfeuer, Shirley has a more compact, broad growth habit, is earlier flowering, has a distinctive bright red flower color, has a longer flowering period and produces more flowers.

The accompanying photographic drawings show typical flower and foliage characteristics of Shirley, with colors being as true as possible with illustrations of this type.

Sheet 1 is a perspective view of a potted plant of Shirley.

Sheet 2 is a black and white print showing the upper surface of immature and mature plants of Shirley.

In the following description color references are made to The Royal Horticultural Society Colour Chart (RHS). The color values were determined at 9:00 a.m. on May 23, 1985 under 35,000 Lux light intensity in a greenhouse at Hillscheid, Federal Republic of Germany.

CLASSIFICATION

Botanical: *Pelargonium domesticum.*

Commercial: Commonly referred to as a "Martha Washington" geranium, and having the cultivar name Shirley.

INFLORESCENCE

A. Umbel:

*Average diameter.*—Relatively small, 85–95 mm.

*Peduncle length.*—Normal.

*Pedicel length.*—Normal.

B. Corolla:

*Average diameter.*—55–65 mm; total inflorescence diameter is within the foliage.

*Form.*—Five-seven petals.

*Color (general tonality from a distance of three meters).*—Red.

*Color (upper surface).*—46B.

C. Bud:

*Shape.*—Elongated.

*Color.*—Red.

D. Reproductive Organs:

*Androecium.*—Yellow-red; 7–10 stamens.

*Gynoecium.*—Five to seven lobed stigma.

E. Spring Flowering Response Period: Early.

G. Durability; Good.

PLANT

A. Foliage:

*Form.*—Zygomorphic with a nectar spur.

*Margin.*—Crenate, indented.

*Color (upper surface).*—Medium green.

*Tolerance of Botrytis and soil fungi.*—Good.

B. General Appearance and Form:

*Internode length.*—Short.

*Branching pattern.*—Excellent.

*Height.*—Compact.

I claim:

1. A new and distinct cultivar of geranium named Shirley, as described and illustrated, and particularly characterized by its bright red flower color; compact, self-branching growth habit; early flowering; good bud production at night temperatures up to 16° C., thus providing a long and continuous flowering period; and ease of propagation and good rooting habit.

* * * * *

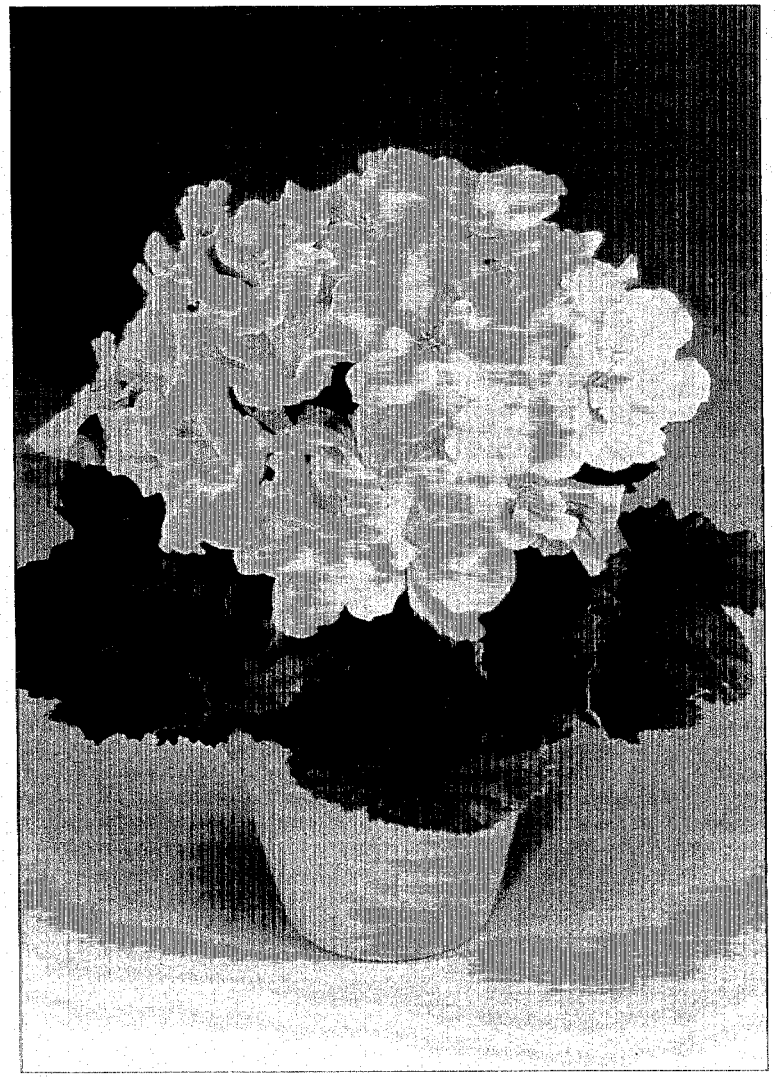

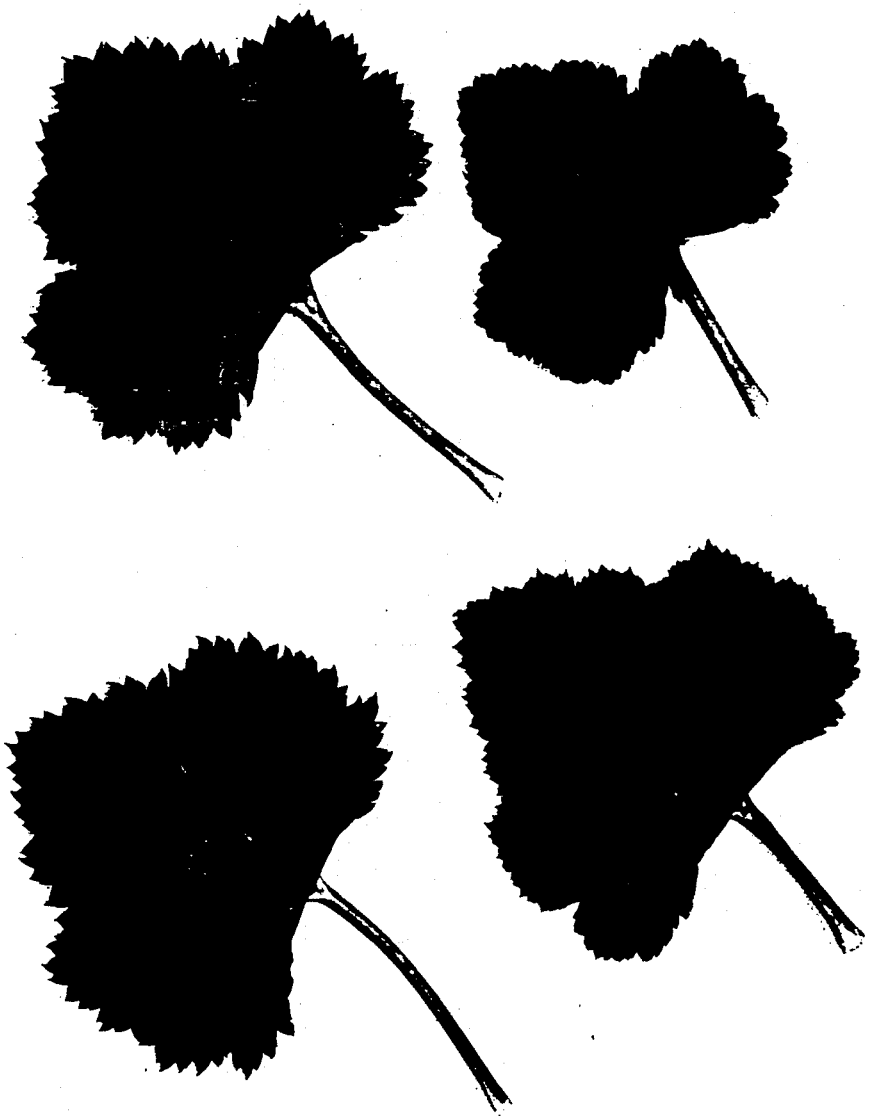

Silvia